(12) United States Patent
Boussignac

(10) Patent No.: US 8,678,004 B2
(45) Date of Patent: Mar. 25, 2014

(54) RESPIRATORY PROBE

(76) Inventor: Georges Boussignac, Antony (FR)

( * ) Notice: Subject to any disclaimer, the term of this patent is extended or adjusted under 35 U.S.C. 154(b) by 1029 days.

(21) Appl. No.: 11/764,437

(22) Filed: Jun. 18, 2007

(65) Prior Publication Data

US 2008/0236591 A1 Oct. 2, 2008

(30) Foreign Application Priority Data

Apr. 2, 2007 (FR) ...................................... 07 02384

(51) Int. Cl.
*A61M 16/04* (2006.01)

(52) U.S. Cl.
USPC ............. 128/207.14; 128/207.16; 128/207.18

(58) Field of Classification Search
USPC ............. 128/207.14, 207.16, 207.18, 206.29, 128/205.19; 604/27, 43, 45
See application file for complete search history.

(56) References Cited

U.S. PATENT DOCUMENTS

| | | | |
|---|---|---|---|
| 2,766,753 A * | 10/1956 | Koch et al. ............... | 128/204.25 |
| 3,527,555 A * | 9/1970 | Schreiber ................. | 128/205.15 |
| 3,815,606 A | 6/1974 | Mazal | |
| 4,265,235 A * | 5/1981 | Fukunaga ................ | 128/200.24 |
| 4,300,550 A * | 11/1981 | Gandi et al. ............. | 128/207.18 |
| 4,676,239 A * | 6/1987 | Humphrey ............... | 128/205.17 |
| 5,335,656 A * | 8/1994 | Bowe et al. ............. | 128/207.18 |
| 5,740,796 A * | 4/1998 | Skog ........................ | 128/204.23 |
| 6,155,252 A | 12/2000 | Warters | |
| 6,398,754 B1 * | 6/2002 | Sutton et al. ..................... | 604/22 |
| 2003/0075176 A1 * | 4/2003 | Fukunaga et al. ........ | 128/203.12 |
| 2004/0231673 A1 * | 11/2004 | Reissmann .............. | 128/207.14 |

FOREIGN PATENT DOCUMENTS

| | | |
|---|---|---|
| EP | 0 747 077 | 12/1996 |
| WO | 01/24861 | 4/2001 |
| WO | 02/94360 | 11/2002 |
| WO | 2006/090043 | 8/2006 |

OTHER PUBLICATIONS

French Preliminary Novelty Search Report dated Nov. 8, 2007 with partial English translation thereof.

* cited by examiner

*Primary Examiner* — Justine Yu
*Assistant Examiner* — Valerie L Skorupa
(74) *Attorney, Agent, or Firm* — Dickinson Wright PLLC

(57) ABSTRACT

A respiratory probe including two channels in parallel, equipped with unidirectional valves connected head-to-tail.

3 Claims, 2 Drawing Sheets

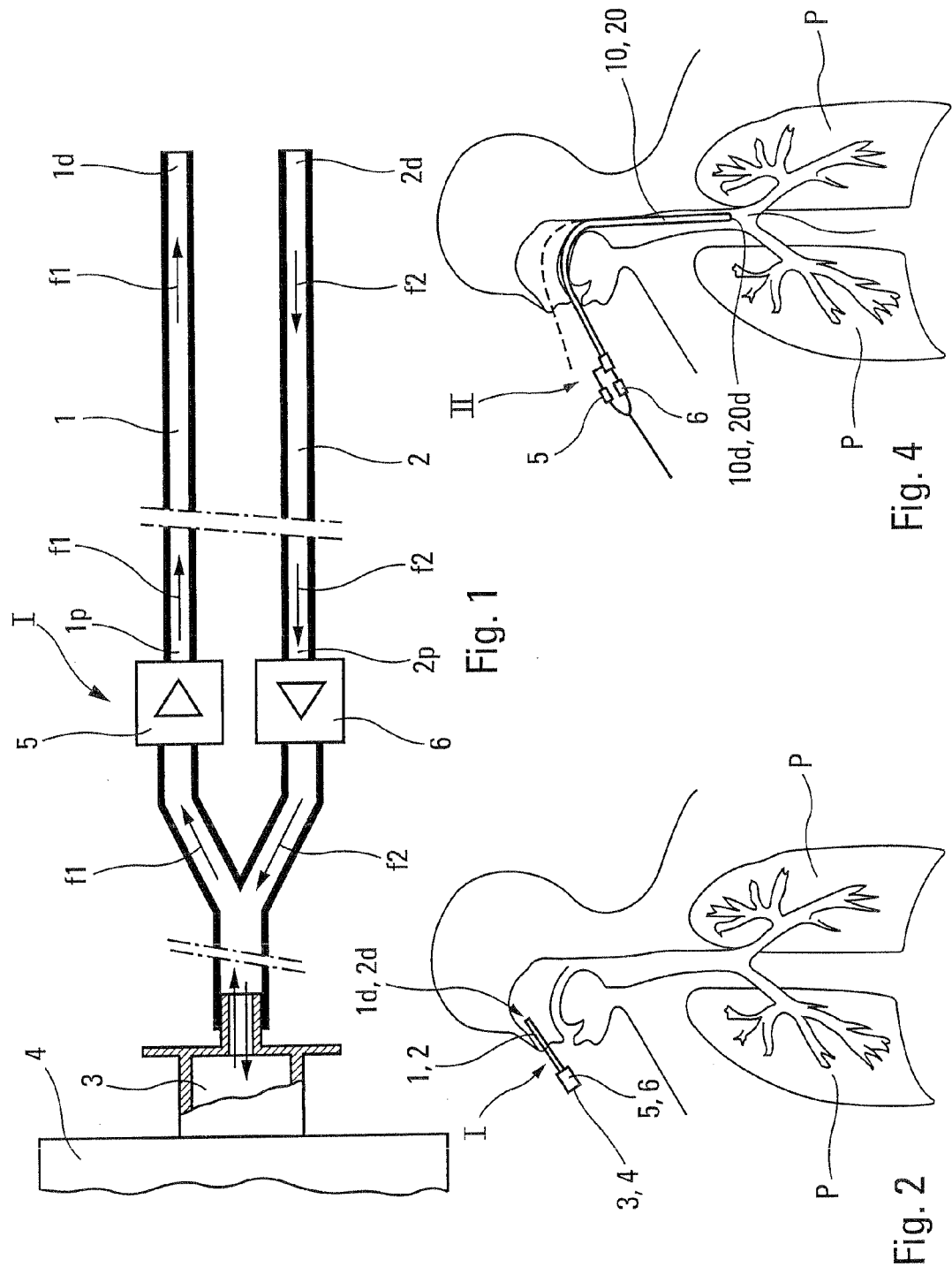

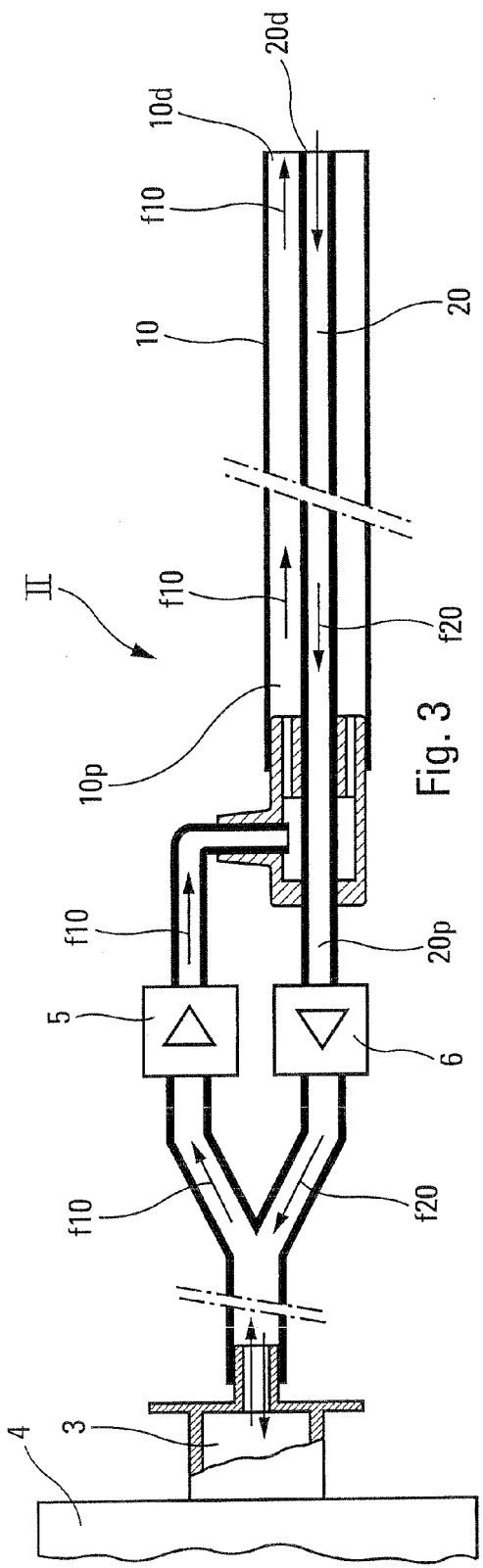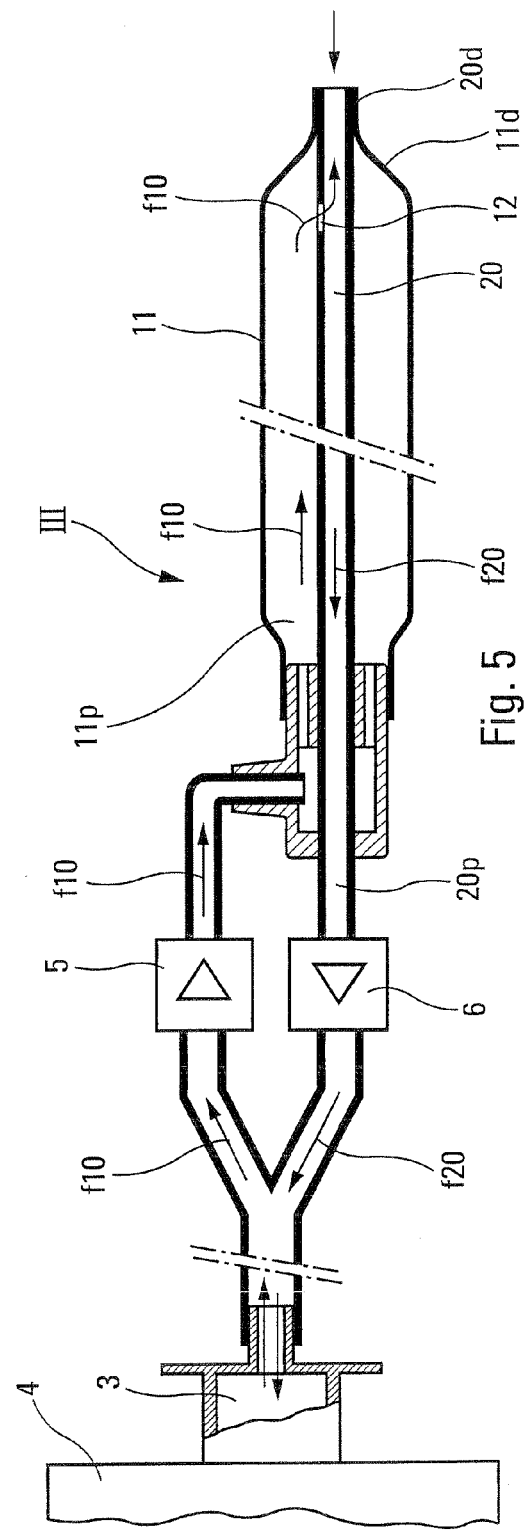

RESPIRATORY PROBE

The present invention relates to a respiratory probe, whose distal end is intended to be inserted in the respiratory system of a patient and whose proximal end is able to be connected to the output of an artificial respirator generating pulses of respiratory gas corresponding to inhalations for said patient.

In respiratory probes of this type, the fresh respiratory gas and the polluted respiratory gas (loaded with carbon dioxide) flow alternately but in opposite directions. Moreover, it is normal that, during exhalations, the totality of the polluted respiratory gas is not evacuated. The result of this is therefore that the non-evacuated polluted respiratory gas opposes the consecutive introduction of fresh respiratory gas, which results in poor oxygenation of the patient. In order to attempt to avoid this disadvantage, the pressure at which said artificial respirator delivers the fresh gas is increased in order to expel the polluted respiratory gas. However, there is then a risk of injuring the patient, particularly if the latter is a child.

The purpose of the present invention is to overcome these disadvantages.

For this purpose, according to the invention, the respiratory probe, whose distal end is intended to be inserted in the respiratory system of a patient and whose proximal end is able to be connected to the output of an artificial respirator at which appear pulses of respiratory gas corresponding to inhalations for said patient, is noteworthy in that:
- said probe comprises two independent channels each provided with a distal end intended to be inserted in said respiratory system and a proximal end able to be connected to the output of said artificial respirator;
- the proximal ends of said channels of the probe are able to be connected in common to said output of the artificial respirator by the intermediary of respective unidirectional valves; and
- one of said unidirectional valves allows flow in the direction from the proximal end towards the distal end of the channel to which it is connected, whilst the other of said unidirectional valves allows flow in the direction from the distal end towards the proximal end of the other one of said channels to which it is connected.

Thus, due to the invention, the residual polluted respiratory gas cannot oppose the introduction of fresh respiratory gas through the respiratory channel provided with the unidirectional value allowing flow from the proximal end towards the distal end. Moreover, nothing opposes the evacuation, through the other respiratory channel, of the possible residual polluted respiratory gas by the action of the introduced fresh respiratory gas. There is therefore no necessity of injecting the respiratory gas at an excessive pressure.

Said channels of the probe can be disposed in parallel or coaxially.

In the latter case, the probe can comprise a central channel constituted by a flexible tube and a peripheral channel constituted by a flexible sleeve surrounding said flexible tube. In an advantageous embodiment, the distal end of the flexible sleeve can be firmly joined to the distal end of said flexible tube and the latter can comprise, in the vicinity of its distal end, at least one traversing passage disposed inside said flexible sleeve.

The probe according to the present invention can be of the buccal or nasal type.

The figures of the appended drawing will give a good understanding of how the invention can be embodied. In these figures, identical references denote similar items.

FIG. 1 shows, in diagrammatic longitudinal cross-section, a first embodiment of the probe according to the present invention.

FIG. 2 shows the insertion, in patient, of the probe shown in FIG. 1, when said probe is of the nasal type.

FIGS. 3 and 5 respectively show, in diagrammatic longitudinal cross-section, two other embodiments of the probe according to the present invention FIG. 4 shows the insertion, in a patient, of the probe shown in FIG. 3 when said probe is of the buccal type.

The respiratory probe I, according to the present invention and shown in FIG. 1, comprises two independent respiratory channels, in parallel, respectively constituted by flexible tubes 1 and 2.

At the proximal end, said tubes 1 and 2 are connected in common to the output 3 of an artificial respirator 4 (shown very partially) by the intermediary of unidirectional valves 5 and 6. The valve 5, fitted to the flexible tube 1, allows flow from the proximal end 1$p$ towards the distal end 1$d$ of said flexible tube 1 and stops flow in the opposite direction. On the contrary, the valve 6 fitted to the flexible tube 2 allows flow from the distal end 2$d$ towards the proximal end 2$p$ of said flexible tube 2 and stops flow in the opposite direction.

Even though the probe I can be of the buccal type, it is particularly appropriate for use as a nasal probe, as shown diagrammatically in FIG. 2. In this figure, the lungs P of a patient have been shown diagrammatically, the distal ends 1$d$ and 2$d$ of said tubes 1 and 2 being respectively inserted in the nostrils of said patient.

Thus, when the artificial respirator 4 sends the probe I a pulse of respiratory gas corresponding to in inhalation for said patient, this pulse is transmitted to said lungs P, through the valve 5 and the tube 1, as indicated by the arrows f1 in FIG. 1.

On the other hand, the polluted respiratory gas, corresponding to a previous pulse of gas and present in the lungs P, is expelled from the latter and sent to the artificial respirator 4 through the tube 2 and the valve 6, as indicated by the arrows f2 in FIG. 1. The artificial respirator 4 detects the arrival of this polluted respiratory gas corresponding to an exhalation of the patient and can send a new pulse of respiratory gas, corresponding to an inhalation, to said lungs P.

It can easily be seen that, due to said probe I, the introduction of respiratory gas into the lungs P of a patient cannot be impeded by the polluted respiratory gas present in said lungs and that, on the contrary, the polluted respiratory gas is eliminated from the latter without difficulty.

FIG. 3 shows a probe II, according to the present invention, in which the two independent respiratory channels, formed by the flexible tubes 10 and 20 respectively, are coaxial, instead of being parallel like the channels 1 and 2 of the probe I. In this FIG. 3, the arrangement 3, 4, 5 and 6 which is described with reference to FIG. 1 and to which the proximal ends 1o$p$ and 20$p$ of said tubes 10 and 20 are connected, is again present.

The probe II could be of the nasal type; however, it is advantageously of the buccal type, as shown in FIG. 4. In fact, in this case, it can en inserted in the respiratory system of the patient until the distal ends 1ed and 20$d$ of the coaxial flexible tubes are in the vicinity of the carina C. Thus, the dead space between the distal end of the probe II and the lungs P is reduced to a minimum.

Thus, when the artificial respirator 4 sends to the probe II a pulse of respiratory gas corresponding to an inhalation for the patient, this pulse is transmitted to the carina C, through the valve 5 and the peripheral tube 10, as indicated by the arrows f10 in FIG. 3.

On the other hand, the polluted respiratory gas present in the lungs P is expelled from the latter, from the carina C and through the central tube 20, as indicated by the arrows f20 in FIG. 3. A new pulse of respiratory gas can then be sent by the artificial respirator 4 (arrows f10) to the lungs P.

FIG. 5 shows a variant embodiment III of the probe II shown in FIG. 3. In the probe III the arrangement 3, 4, 5, 6 and 20 described above are again present. On the other hand, the peripheral tube 10 is replaced by a flexible sleeve 11 which surrounds the central tube 20 and whose proximal end 11p is connected to the valve 5. The distal end 1id of the flexible sleeve 11 is firmly joined in a fluid-tight manner to the distal end 20d of said tube 20d and said tube 20 comprises, in the vicinity of its distal end 20d, a traversing passage 12, located inside the flexible sleeve 11. In this case, the pulses of respiratory gas (arrows f10) generated by the artificial respirator 4 traverse the passage 12 and are sent to the lungs through the distal end 20d of the central tube 20. It will easily be understood that the probe III can be used in a similar manner to that of the probe II, as shown in FIG. 4.

The invention claimed is:

1. A respiratory probe, whose distal end is for being inserted in a respiratory system of a patient and whose proximal end is for being connected to a single input/output of an artificial respirator at which appear pulses of respiratory gas corresponding to exhalations and inhalations of said patient, comprising:

two independent channels, provided with a single input/output distal end for inserting into said patient's respiratory system and with a proximal end to the single input/output of the artificial respirator, the proximal ends of said independent channels being connected in common to said single input/output of the artificial respirator through an intermediary comprised of respective unidirectional valves, wherein one of the unidirectional valves is fitted to one of the independent channels and allows flow of the respiratory gas pulsed from the single input/output of the artificial respirator at the proximal end towards the distal end of the independent channel to the patient for inhalation, and the other of the unidirectional valves is fitted to the other independent channel and allows flow of exhalations from the patient at the distal end towards the proximal end of the other independent channel into the single input/output of the artificial respirator, wherein the two channels of the probe are coaxial and comprise:

a central channel constituted by a flexible tube; and a peripheral channel constituted by a flexible sleeve surrounding said flexible tube, and wherein a distal end of said flexible sleeve is joined in a fluid tight manner to a distal end of said flexible tube and wherein said flexible tube comprises at least one traversing passage disposed inside said flexible sleeve providing distal end communication between the central and peripheral channels.

2. The probe as claimed in claim 1, wherein the probe is of the buccal type.

3. The probe as claimed in claim 1, wherein the probe is of the nasal type.

* * * * *